United States Patent
Yasui et al.

(10) Patent No.: US 6,294,669 B1
(45) Date of Patent: Sep. 25, 2001

(54) CRYSTALLINE SUBSTANCE OF CEFDITOREN PIVOXYL AND THE PRODUCTION OF THE SAME

(75) Inventors: Kiyoshi Yasui; Masahiro Onodera; Masamichi Sukegawa; Tatsuo Watanabe, all of Odawara; Yuichi Yamamoto, Motosu-gun; Yasushi Murai; Katsuharu Iinuma, both of Odawara, all of (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 0 days.

(21) Appl. No.: 09/269,109

(22) PCT Filed: Sep. 19, 1997

(86) PCT No.: PCT/JP97/03340

§ 371 Date: Mar. 19, 1999

§ 102(e) Date: Mar. 19, 1999

(87) PCT Pub. No.: WO98/12200

PCT Pub. Date: Mar. 26, 1998

(30) Foreign Application Priority Data

Sep. 20, 1996 (JP) .................................................. 8-249561

(51) Int. Cl.[7] ................................................. C07D 501/24
(52) U.S. Cl. .............................................................. 540/227
(58) Field of Search ............................................. 540/227

(56) References Cited

U.S. PATENT DOCUMENTS 5,616,703 * 4/1997 Ludescher ............................. 540/227
5,827,845 * 10/1998 Shiokawa ............................... 540/227

FOREIGN PATENT DOCUMENTS

175610 * 3/1986 (EP) .

OTHER PUBLICATIONS

Sakagami, J. Antibiotics 43 (8), 1047, Aug. 1990.*
Sakagami, Chem Pharm. Bull. 39(9) 2433, Sep. 1991.*

* cited by examiner

*Primary Examiner*—Mark L. Berch
(74) *Attorney, Agent, or Firm*—Larson & Taylor PLC

(57) ABSTRACT

As a novel substance is provided such a new, crystalline substance of Cefditoren povoxyl which has a high purity and an enhanced thermal stability on storage. This crystalline Cefditoren pivoxyl may be prepared by a process comprising a step of dissolving amorphous substance of Cefditoren pivoxyl in an anhydrous, first organic solvent capable of dissolving said amorphous substance well therein, and steps of replacing the first organic solvent component of the resulting solution by an anhydrous alkanol of 1 to 5 carbon atoms as a second organic solvent, in such a manner that the firstly prepared solution of Cefditoren pivoxyl in the first organic solvent is mixed with a volume of the alkanol and then is concentrated below 15° C. under reduced pressure, and so on. Thereby, the process proceeds so as to produce a solution containing 50 mg/ml to 250 mg/ml of Cefditoren pivoxyl dissolved in the alkanol alone. From the latter solution, crystals of Cefditoren pivoxyl are induced to deposit by addition of water at a temperature of 0–10° C. The resulting admixture of the concentrated solution of Cefditoren pivoxyl in alkanol with added water and the deposited Cefditoren pivoxyl is then agitated 10° C. or below, to effect a complete crystallization of Cefditoren pivoxyl.

6 Claims, 13 Drawing Sheets

CRYSTALLINE SUBSTANCE OF CEFDITOREN PIVOXYL AND THE PRODUCTION OF THE SAME

This application is a 371 application of PCT/JP97/03340, filed Sep. 19, 1997.

TECHNICAL FIELD

This invention relates to a new, crystalline substance of Cefditoren pivoxyl and also relates to new processes for the production of the new, crystalline substance of Cefditoren pivoxyl. Cefditoren pivoxyl is an orally administrable pro-drug which belongs to an antibacterially active antibiotic of cephalosporin-type and is a compound usually named as 7-[(Z)-2-(2-amino-thiazol-4-yl)-2-methoxyiminoacetamido]-3-[(Z)-2-(4-methylthiazol-5-yl) ethenyl]-3-cephem-4-carboxylic acid pivaloyloxymethyl ester.

BACKGROUND ART OF INVENTION

Cefditoren is a cephem compound which is represented by the following formula (A):

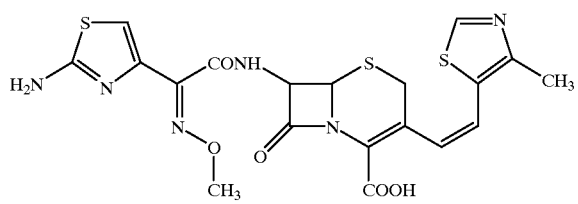

(A)

and named as (+)-(6R,7R)-7-[(Z)-2-(2-aminothiazol-4-yl)-2-methoxyiminoacetamido]-3-[(Z)-2-(4-methylthiazol-5-yl)-ethenyl]-8-oxo-5-thia-1-azabicyclo[4.2.0]oct-2-ene-2-carboxylic acid. This cephem compound of the generic name "Cefditoren" is also nominated as 7-[2-methoxyimino-2-(2-aminothiazol-4-yl)acetamido]-3-[2-(4-methylthiazol-5-yl) vinyl]-3-cephem-4-carboxylic acid(syn-isomer, cis-isomer) in Japanese patent No. 1698887(Japanese patent publication "Kokoku" No. Hei-3-64503 published on Oct. 7, 1991), U.S. Pat. No. 4,839,350 and European patent No. 0175610.

A pivaloyloxymethyl ester of Cefditoren, in which the 4-carboxyl group has been esterified with the pivaloyloxymethyl group for the purpose of enhancing the absorbability of the cephem compound via the digestive tubes upon the oral administration thereof, is such a pro-drug which is known by a generic name "Cefditoren pivoxyl" and is represented by the following formula (B):

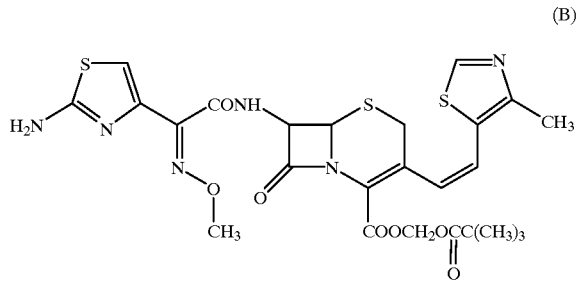

(B)

and which has a chemical name "(–)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo-[4.2.0]oct-2-ene-2-carboxylic acid 2,2-dimethylpropionyl-oxymethyl ester". Cefditoren pivoxyl is known to be a pale yellow colored and powdery substance having a melting point of 127 to 129° C. (see the "Merck Index", 12th-edition, page 317).

Cefditoren has a low toxicity to mammals but exhibits a very much broad antibacterial spectrum against gram-positive-bacteria and gram-negative bacteria. Cefditoren pivoxyl is, by itself, antibacterially inactive but is useful as a pro-drug which is adminstrable orally and can be converted into the antibacterially active Cefditoren in the digestive tubes of mammals, with cleaving the ester-forming pivaloyloxymethyl group therefrom. Cefditoren and Cefditoren pivoxyl are known to be a highly excellent therapeutic agent which has extensively been utilized for the therapeutic treatments and preventive treatments of bacterial infections caused by a variety of gram-positive bacteria and gram-negative bacteria.

Such products of Cefditoren pivoxyl which are produced and available commercially at present are usually and exclusively in the form of an amorphous and powdery substance. This amorphous substance of Cefditoren pivoxyl is usually prepared by such a method in which a reaction solution containing Cefditoren pivoxyl as synthetized is mixed with isopropyl ether to precipitate an amorphous powder of Cefditoren pivoxyl and this amorphous powder of Cefditoren pivoxyl is dissolved in methanol, and in which the resulting solution tion of Cefditoren pivoxyl in methanol is added with aqueous isopropanol to precipitate an amorphous powder of Cefditoren pivoxyl and this amorphous powder is then recovered (see, for example, Example 2 of U.S. Pat. No. 4,839,350 and European patent No. 0175610).

Thus, hitherto, any crystalline substance or form of Cefditoren pivoxyl has neither been known nor obtained, as far as we have been aware of. The known, amorphous substance of Cefditoren pivoxyl has widely been utilized as an excellent, antibiotic drug, as stated in the above, but it is not yet a completely satisfactory drug in that it is not stable to a sufficient extent when stored at an elevated temperature and under highly humid conditions. Besides, it has been found that the presently commercially available, amorphous substance of Cefditoren pivoxyl usually has a purity of 94% to 95.5% for the Cefditoren pivoxyl component when analysed by a liguid chromatography on a reverse phase silica gel column as detected with a ultra-violet ray absorption.

Accordingly, there exists an outstanding demand to provide such a new product of Cefditoren pivoxyl which would be much more pure and much more stable than the known, amorphous substance of Cefditoren pivoxyl. There is further presented an another demand to provide such a new process which is able to produce a highly pure product of Cefditoren pivoxyl in an efficient way on a commercial scale.

DISCLOSURE OF INVENTION

We, the present inventors, have conducted extensive investigations in order to solve the above-mentioned problems, and we have then presumed that, if Cefditoren pivoxyl can be obtained in a crystalline form, it will be a much more highly pure and stable product.

The present inventors have thus made further investigations in an attempt to produce a crystalline form of Cefditoren pivoxyl. As a result of these further investigations, we have now found that, when an amorphous substance of Cefditoren pivoxyl is once dissolved in an anhydrous, first organic solvent which can dissolve well the amorphous Cefditoren pivoxyl therein, and when the resulting solution of Cefditoren pivoxyl in said first organic solvent is concentrated to a reduced volume of the solution at a temperature of not higher than 15° C. by evaporation of the first organic solvent under a reduced pressure, followed by admixing the resultant concentrated solution with a volume of a anhydrous alkanol containing 1 to 5 carbon atoms, as a second organic solvent miscible with the first organic solvent, and then by repeating several times the concentration tration of the solution and the admixing of the concentrated solution with further amounts of the alkanol of 1 to 5 carbon atoms at a temperature of not higher than 15° C., in such an ingenious way as detailed hereinafter, thereby to prepare a concentrated solution containing 50 to 250 mg/ml of Cefditoren pivoxyl dissolved in substantially only one second organic solvent, the alkanol, and when the resultant concentrated solution containing 50 to 250 mg/ml of Cefditoren pivoxyl in the alkanol is subsequently mixed with a volume of water at a temperature ture of not higher than 10° C., then Cefditoren pivoxyl can start to deposit in a crystalline particle form from said concentrated solution and a complete crystallization of Cefditoren pivoxyl can be achieved by agitation of the aqueous mixture of the remaining solution with the deposited crystal particles, at a temperature of 10° C. or below, and a crystalline substance of Cefditoren pivoxyl can be separated and harvested from the remaining solution (the liquid phase) by filtration or centrifugation.

Thus, the present inventors, have now succeeded in obtaining such a crystalline substance of Cefditoren pivoxyl which has a high purity of 97% to 98% for the Cefditoren pivoxyl component and can exhibit a remarkably higher storage stability at an elevated temperature, as compared with the known, amorphous substance of Cefditoren povoxyl.

This crystalline substance of Cefditoren pivoxyl now obtained is in the orthorhombic form as measured by an X-ray powder diffractometer and an X-ray single-crystal diffractometer, and said crystalline substance of Cefditoren pivoxyl comprises single crystals having a density of 1.21 to 1.23 g/cm$^3$. This crystalline substance of Cefditoren pivoxyl further has a melting point of 206.2° C. to 215.7° C. with decomposition, as evaluated from the peak of thermal absorption shown in such a heat flow curve which was determined by testing the crystalline substance in a differential scanning calorimeter. It is considered that this crystalline substance of Cefditoren pivoxyl having the orthorhombic form and having the above-mentioned physico-chemical characteristics should be a novel substance, since any product or substance of Cefditoren pivoxyl which exhibits the above identified particular physico-chemical characteristic was never known in the past.

Furthermore, the present inventors have now found that the new, crystalline substance of Cefditoren pivoxyl now obtained is tasteless to tongue when placed on the tongue, contrarily to that the known amorphous substance of Cefditoren pivoxyl normally gives an objectionably bitter taste to tongue, when it is given orally (see an internationally published specification No. WO 97/13516 of PCT application No. PCT/JP 96/02967).

This invention has now been accomplished on the basis of the above-mentioned findings of the present inventors.

In a first aspect of this invention, therefore, there is provided, as a novel substance, a crystalline substance of Cefditoren pivoxyl, namely 7-[(Z)-2-(2-aminothiazol-4-yl)-2-methoxyiminoacetamido]-3-[(Z)-2-(4-methylthiazol-5-yl) ethenyl]-3-cephem-4-carboxylic acid pivaloyloxymethyl ester, characterized in that said crystalline substance of Cefditoren pivoxyl is of orthorhombic form and has a melting point with decomposition at a temperature in a range of 206.2° C. to 215.7° C. as evaluated from the peak of thermal absorption shown in the heat flow curve of said substance determined with a differential scanning calorimeter, that a single crystal of said crystalline substance has a density of 1.21 to 1.23 g/cm$^3$ and contains 4 molecules of Cefditoren pivoxyl within a unit lattice of the single crystal, that said crystalline substance has a purity of 97% to 98% for the Cefditoren pivoxyl component as measured by a liquid chromatography with using a reverse phase silca gel column and by detecting with ultra-violet ray absorption, and that said crystalline substance has a higher thermal stability than the known amorphous substance of Cefditoren pivoxyl.

It is preferred that the crystalline substance of Cefditoren pivoxyl has a purity of 97.7% or higher for the Cefditoren pivoxyl component.

Several samples of the new crystalline substance of Cefditoren pivoxyl provided in accordance with the first aspect of this invention were taken and were analysed by an X-ray powder diffractometer, and it is then found that X-ray powder diffractometer data of the tested crystalline substance of Cefditoren pivoxyl shows the diffraction peaks at the following diffraction angles:

approximately 9.7 degree, approximately 10.8 degree, approximately 11.4 degree, approximately 12.1 degree, approximately 13.6 degree, approximately 15.6 degree, approximately 16.2 degree, approximately 17.4 degree, approximately 19.0 degree, approximately 19.5 degree, approximately 20.1 degree, approximately 20.8 degree, approximately 21.5 degree, approximately 25.2 degree, approximately 29.9 degree and approximately 33.0 degree. It is to be added that the known, amorphous substance of Cefditoren pivoxyl does not show any peak of the diffraction when tested by the same X-ray powder diffractometer as above.

Further, a single crystal was taken as a sample from the crystalline product of Cefditoren pivoxyl which was produced in Example 1 given hereinafter, and the crystal structure of this single crystal was investigated using an X-ray single-crystal diffractometer (Model, AFC-5R, a product of Rigaku-Denki Company, Ltd., Japan). As a result, it is found that the tested single crystal of Cefditoren pivoxyl has substantially the crystallographic features as tabulated in Table 1 below.

TABLE 1

Crystallographic data of a single crystal of Cefditoren pivoxyl

| | |
|---|---|
| Crystalline system: | Orthorhombic form |
| Lattice constants: | a = 14.026Å, b = 18.438Å, c = 11.815Å |
| | α = 90°, β = 90°, γ = 90°, |
| Space group: | P2$_1$ P2$_1$ P2$_1$, |
| Number of molecules within a single unit lattice: | 4 |
| Lattice capacity: | 3055 Å$^3$ |
| Density: | 1.22 g/cm$^3$ on average, |
| R value: | 4% |

The above-mentioned crystallographic data of the single crystal of Cefditoren pivoxyl now reveal that one molecule of Cefditoren pivoxyl present in one unit lattice of the crystal takes such a molecular conformation of the molecule as depicted in FIG. 1 of the accompanying drawings. From the above data, it is further revealed that the stereo-chemistry in the oxime moiety and the stero-chemistry at the 3-position of the Cefditoren pivoxyl compound having the crystalline form are evidently of the Z-configuration, and thus are of the syn-configuration and of the Z-configuration, respectively, indicating that the crystalline substance of Cefditoren pivoxyl as obtained according to this invention should certainly be a crystalline 7-[(Z)-2-(2-aminothiazol-4-yl)-2-methoxyiminoacetamido]-3-[(Z)-2-(4-methylthiazol-5-yl)ethenyl]-3-cephem-4-carboxylic acid pivaloyloxymethyl ester.

As described hereinbefore, the new, crystalline substance of Cefditoren pivoxyl according to this invention has an improved storage stability than the known amorphous form of Cefditoren pivoxyl.

In order to test the thermal stability on storage of the new crystalline substance of Cefditoren pivoxyl according to this invention, in comparison with the known, amorphous form of Cefditoren pivoxyl, there were employed a sample of the crystalline Cefditoren pivoxyl which was produced in Example 1 given hereinafter, as well as a sample of the amorphous Cefditoren pivoxyl which was produced by admixing a solution of amorphous Cefditoren pivoxyl in methanol with an aqueous iso-propanol to precipitate an amorphous powder of this compound and separating and drying this powder under a reduced pressure. These samples were separately placed in sealed dry containers and were stored for 1 month, for 2 months and for 4 months at 60° C. and at 40° C., respectively. After these storages, the samples were analysed by a liquid chromatographic method and percentages of the residual quantity of Cefditoren pivoxyl remaining in the stored samples were evaluated from the area under the absorption peak which was shown in the chromatogramms obtained. It is assumed that the initial content of Cefditoren pivoxyl in the test samples was 100% at the starting of the storages.

The test results obtained are summarized in Tables 2 and 3 below.

TABLE 2

| | Residual quantity (%) of Cefditoren pivoxyl upon storage at 60° C. | | |
| --- | --- | --- | --- |
| Test sample | Initial content (at 0 day) | After 1 month | After 2 months |
| Crystalline substance | 100% | 99% | 99% |
| Amorphous substance | 100% | 93% | 88% |

TABLE 3

| | Residual quantity (%) of Cefditoren pivoxyl upon storage at 40° C. | | | |
| --- | --- | --- | --- | --- |
| Test sample | Initial content (at 0 day) | After 1 month | After 2 months | After 4 months |
| Crystalline substance | 100% | 100% | 100% | 99% |
| Amorphous substance | 100% | 99% | 99% | 96% |

From the results of Tables 2 and 3 above, it is observed that the crystalline substance of Cefditoren pivoxyl according to this invention is able to have a residual quantity of Cefditoren pivoxyl of 99% even after the 4-month storage at 40° C. and also after the 2-month storage at elevated temperatures of up to 60° C., indicating that the residual quantity of Cefditoren pivoxyl does not decrease substantially for a long time upon storage of the crystalline Cefditoren pivoxyl under ordinary conditions at ambient temperatures, and that the crystalline Cefditoren pivoxyl of this invention has a better thermal stability than the known, amorphous Cefditoren pivoxyl.

Next, the production of the crystalline substance of Cefditoren pivoxyl according to this invention will be described.

When briefly speaking, the crystalline substance of Cefditoren pivoxyl may be produced by such a process which is characterized by comprising a step of dissolving an amorphous substance of Cefditoren pivoxyl into an anhydrous first organic solvent capable of dissolving Cefditoren pivoxyl well therein than an alkanol of 1 to 5 carbon atoms, and a step of subsequently replacing the first organic solvent component of the resulting solution stepwise by some proportions of an anhydrous alkanol of 1 to 5 carbon atoms as a second organic solvent, in such a manner that the firstly prepared solution of Cefditoren pivoxyl in the first organic solvent is admixed with a proportion of an anhydrous alkanol (the second organic solvent), the resulting admixture is concentrated to a reduced volume by evaporation of the first and second organic solvent therefrom under a reduced pressure, whereby a concentrated solution of Cefditoren pivoxyl in a mixed solvent comprising a smaller proportion of the first organic solvent and a larger proportion of the alkanol (the second organic solvent) is formed, this concentrated solution is again admixed with a further amount of the alkanol and then again concentrated by evaporation of the first and second organic solvents, while the admixing of the concentrated solution with further amount of the alkanol and the concentration of the solution as diluted with the added alkanol are several times repeated, so that there is formed a solution containing at a given concentration of 50 mg–250 mg/ml the Cefditoren pivoxyl dissolved in the solvent solely or substantially solely made of said alkanol, and which process is further characterized by comprising additional step of mixing the latter solution of Cefditoren pivoxyl in the sole alkanol solvent so formed, with a proportion of water at a temperature of not higher than 10° C., to make solid particles of Cefditoren pivoxyl to start to deposit in said solution, and a further step of incubating under agitation the solution containing the solid particles so deposited, at a temperature of 0° C. to 10° C. for a time of 10 minutes to 48 hours so that all the deposited solid particles are crystallized completely in the crystalline form of Cefditoren pivoxyl.

More particularly, in a second aspect of this invention, there is provided a process for the preparation of a crystalline substance of Cefditoren pivoxyl having the orthorhombic form, which comprises conducting successively the following first to eighth steps:

in a first step, dissolving an amorphous substance of Cefditoren pivoxyl in an anhydrous, first organic solvent in which Cefditoren pivoxyl is much more soluble than in an alkanol containing 1 to 5 carbon atoms and which is miscible with the alkanol of 1–5 carbon atoms, thereby to obtain a solution containing 10 mg to 50 mg of the dissolved Cefditoren pivoxyl per 1 ml of the resulting solution of Cefditoren pivoxyl in the first organic solvent, in a second step, mixing the resulting solution of Cefditoren pivoxyl in the first organic solvent with an anhydrous alkanol containing 1 to 5 carbon atoms as a second organic solvent in such a proportion thereof necessary to reduce the concentration of the Cefditoren pivoxyl dissolved in the resulting mixture of said solution of Cefditoren pivoxyl with the second organic solvent to a concentration of 5 mg to 40 mg of the dissolved Cefditoren pivoxyl per 1 ml of said resulting mixture, in a third step, concentrating the resulting solution of Cefditoren pivoxyl in the mixed first and second organic solvents as obtained in the second step, at a temperature of −5° C. to 15° C. by evaporation of the organic solvents from said solution under a reduced pressure, to give a concentrated solution containing 50 mg/ml to 250 mg/ml of the dissolved Cefditoren pivoxyl, in a fourth step, mixing the concentrated solution so obtained in the third step with a further volume of an alkanol of 1 to 5 carbon atoms used as the second organic solvent in such a proportion thereof necessary to reduce the concentration of the Cefditoren pivoxyl dissolved in the resulting mixture of said concentrated solution with the further volume of the alkanol, to a concentration of 25 mg to 125 mg of the dissolved Cefditoren pivoxyl per 1 ml of said resulting mixture, in a fifth step, concentrating the resulting solution of Cefditoren pivoxyl so diluted with the further volume of the alkanol in the fourth step, at a temperature of −5° C. to 15° C. by evaporation of the solvents from said solution under a reduced pressure, to give a concentrated solution containing 50 mg/ml to 250 mg/ml of the Cefditoren pivoxyl dissolved in the solvent entirely or substantially entirely made of said alkanol, in a sixth step, mixing the concentrated solution obtained in the fifth step gradually with water of a volume of 1-fold to 20-folds greater than the volume of the above concentrated solution at a temperature of 0° C. to 10° C., to make Cefditoren pivoxyl to start to deposit as crystals, in a seventh step, agitating the resulting mixture of the above mentioned concentrated solution with water and the deposited crystals as obtained in the sixth step, at a temperature of 0° C. to 10° C. for a time sufficient to effect a complete crystallization of Cefditoren pivoxyl, and in an eighth step, separating and harvesting the crystalline Cefditoren pivoxyl from the remaining solution by filtration or centrifugation, followed by drying the harvested crystalline Cefditoren pivoxyl substance under a reduced pressure.

In the process according to the second aspect of this invention, it is preferred that the first organic solvent used in the first step is chosen from ethylene glycol, propylene glycol, acetone, methyl ethyl ketone, methyl iso-butyl ketone, tetrahydrofuran, dioxane, acetonirile, a lower alkyl ester of acetic acid, particularly methyl acetate, ethyl acetate, and n-propyl acetate, methylene chloride and chloroform, as well as mixed solvents of two or more of them, and that the alkanol as the second organic solvent used in the second step and fourth step is chosen from methanol, ethanol, n-propanol, iso-propanol, n-butanol, iso-butanol, sec-butanol, tert-butanol, n-amyl alcohol, iso-amyl alcohol, sec-amyl alcohol and tert-amyl alcohol, as well as mixed solvents of two or more of them.

In the process according to the second aspect of this invention, it is also preferred that the third step and the fifth step of concentrating the solution of Cefditoren pivoxyl in the solvent(s) is conducted at a temperature of 0° C. to 10° C. under a reduced pressure of 10–50 Torr (guage).

In this process, it is possible that the sixth step of mixing the concentrated solution obtained in the fifth step with water is omitted, but the concentrated solution obtained in the fifth step is immediately agitated at a temperature of 0° C. to 10° C. for a time sufficient to effect a complete crystallization of Cefditoren pivoxyl, and the resultant crystals are subsequently separated and harvested by filtration or centrifugation and then dried under reduced pressure.

In the seventh step of the process according to the first aspect of this invention, the mixture of the concentrated solution of the dissolved Cefditoren pivoxyl with water and the deposited crystals of Cefditoren pivoxyl which have been produced in the sixth step of the process is agitated at a temperature of 0° C. to 10° C. for a time sufficient to effect a complete crystallization of Cefditoren pivoxyl. The agitation may be effected by means of a mechanical agitator or under ultra-sonic irradiation. By the term "to effect a complete crystallization of Cefditoren pivoxyl" is meant that amorphous solid particles of Cefditoren pivoxyl as possibly deposited, if any, can be converted into the crystalline form during the agitation of said mixture so as to prevent a final product of the crystalline Cefditoren pivoxyl from being contaminated with a trace quantity of the amorphous Cefditoren pivoxyl, and also that the Cefditoren pivoxyl solute present in the solution is made deposited to a complete extent or a maximum extent as much as possible.

Once the crystalline substance of Cefditoren pivoxyl has been obtained successfully in accordance with the process of the second aspect of this invention, the crystalline substance of Cefditoren pivoxyl may be produced by a different process which utilizes said crystalline substance of Cefditoren pivoxyl as a seed crystal and comprises some steps of the process of the second aspect of this invention.

In a third aspect of this invention, thus, there is provided a process for the preparation of a crystalline substance of Cefditoren pivoxyl having the orthorhombic form, which comprises conducting successively the following steps (a) to (i):

(a) effecting the process of the second aspect of this invention as described hereinbefore, thereby to obtain a crystalline substance of Cefditoren pivoxyl having the orthorhombic form, (b) placing the so obtained crystalline substance of Cefditoren pivoxyl as a seed crystal in a solution containing 10 mg/ml to 50 mg/ml of Cefditoren pivoxyl which has been prepared by dissolution of an amorphous substance of Cefditoren pivoxyl in an anhydrous, first organic solvent as defined above, (c) incubating the solution of Cefditoren pivoxyl in the first organic solvent and further containing therein the seed crystal of Cefditoren pivoxyl added in the above step (b), at a temperature of 0° C. to 50° C. for a time of 10 minutes to 48 hours, preferably at a temperature of 0° C. to 20° C. for a time of 20 hours to 40 hours, to make a crystalline substance of Cefditoren pivoxyl to start to deposit from said solution.

(d) concentrating the solution of Cefditoren pivoxyl with the seed crystal so incubated in the above step (c), at a temperature of −5° C. to 15° C. by evaporation of the first organic solvent therefrom under a reduced pressure, thereby to give a concentrated solution containing 50 mg/ml to 250 mg/ml of the dissolved Cefditoren pivoxyl and the seed crystal of Cefditoren pivoxyl remaining therein, (e) mixing the concentrated solution of Cefditoren pivoxyl containing the remaining seed crystal as obtained in the above step (d) with an anhydrous alkanol of 1 to 5 carbon atoms as the second organic solvent in a proportion thereof necessary to reduce the concentration of the dissolved Cefditoren pivoxyl to a concentration of 25 mg/ml to 125 mg/ml of the Cefditoren pivoxyl dissolved in the resulting mixture of said concentrated solution of Cefditoren pivoxyl with the alkanol which still contains the remaining seed crystal of Cefditoren pivoxyl, (f) concentrating the resulting mixture of the concentrated solution of Cefditoren pivoxyl with the alkanol as obtained in the above step (e), at a temperature of −5° C. to 15° C. by evaporation of the first organic solvent and the alkanol therefrom under a reduced pressure, thereby to give a concentrated solution containing the dissolved Cefditoren pivoxyl at its concentration of 50 mg/ml to 250 mg/ml and the remaining seed crystal of Cefditoren pivoxyl, (g) mixing the concentrated solution comprising the dissolved Cefditoren pivoxyl and the remaining seed crystal as obtained in the above step (f), with water of a volume of 1-fold to 20-folds greater than the volume of said concentrated solution of Cefditoren pivoxyl, at a temperature of 0° C. to 10° C., thereby to facilitate a crystalline substance of Cefditoren pivoxyl to deposit from the resulting mixture of said concentrated solution of Cefditoren pivoxyl with water, (h) agitating the resulting aqueous mixture of the solution containing the dissolved Cefditoren pivoxyl, water and the deposited crystalline substance of Cefditoren pivoxyl as obtained in the above step (g), at a temperature of 0° C. to 10° C., for a time of 20 hours to 40 hours, thereby to effect a complete crystallization of the Cefditoren pivoxyl, and (i) separating and harvesting the crystals obtained in the above step (h), from the remaining solution, followed by drying the harvested crystals under a reduced pressure.

In the process according to the third aspect of this invention, it is preferred that the solution of Cefditoren pivoxyl in the anhydrous first organic solvent to be added with the seed crystal of Cefditoren pivoxyl in the step (b) is such solution that has been prepared by dissolution of the amorphous substance of Cefditoren pivoxyl in an organic solvent chosen from ethylene glycol, propylene glycol, acetone, methyl ethyl ketone, methyl iso-butyl ketone, tetrahydrofuran, dioxane, acetonirile, a lower alkyl ester of acetic acid, particularly methyl acetate, ethyl acetate, and n-propyl acetate, methylene chloride and chloroform, as well as mixed solvents of two or more of them, and that the alkanol used in the step (e) is chosen from methanol, ethanol, n-propanol, iso-propanol, n-butanol, iso-butanol, sec-butanol, tert-butanol, n-amyl alcohol, iso-amyl alcohol, sec-amyl alcohol and tert-amyl alcohol, as well as mixed solvents of two or more of them.

In this process, it is also preferred that the step (c) of incubating the solution of Cefditoren pivoxyl containing the seed crystal, as well as the steps (d) and (f) of concentrating the solution of Cefditoren pivoxyl are effected at a temperature of not higher than 10° C.

The crystalline substance of Cefditoren pivoxyl according to the first aspect of this invention may be produced also by another process which comprises much more reduced steps than in the processes of the second and third aspects of this invention, with utilizing as a seed crystal such a crystalline Cefditoren pivoxyl as prepared previously.

In a fourth aspect of this invention, there is provided a process for the preparation of a crystalline substance of Cefditoren pivoxyl having the orthorhombic form, which comprises consecutively conducting the following steps (i) to (iv):

(i) a step of effecting the process of the first aspect invention, thereby to obtain a crystalline substance of Cefditoren pivoxyl having the orthorhombic form, (ii) a step of placing the crystalline substance of Cefditoren pivoxyl obtained in the step (i), as a seed crystal in a solution of Cefditoren pivoxyl which has been prepared by dissolution of an amorphous substance of Cefditoren pivoxyl to a concentration of 10 mg/ml to 50 mg/ml in an anhydrous organic solvent chosen from ethylene glycol, propylene glycol, acetone, methyl ethyl ketone, methyl iso-butyl ketone, tetrahydrofuran, dioxane, acetonirile, a lower alkyl ester of acetic acid, particularly methyl acetate, ethyl acetate, and n-propyl acetate, methylene chloride, chloroform, and mixed solvents of two or more of them, as well as methanol, ethanol, n-propanol, iso-propanol, n-butanol, iso-butanol, sec-butanol, tert-butanol, n-amyl alcohol, iso-amyl alcohol, sec-amyl alcohol, tert-amyl alcohol, and mixed solvents of two or more of them.

(iii) a step of agitating the resulting mixture of the solution of Cefditoren pivoxyl in the organic solvent with the seed crystal of Cefditoren pivoxyl as obtained in the step (ii), at a temperature of not higher than 50° C., for a time sufficient to facilitate the crystallization of the Cefditoren pivoxyl in the solution, and (iv) separating and harvesting the deposited crystalline substance of Cefditoren pivoxyl from the remaining solution by filtration or centrifugation, followed by drying the harvested crystals of Cefditoren pivoxyl under a reduced pressure.

BRIEF DESCRIPTION OF ACCOMPANYING DRAWINGS

BEST MODE FOR CARRYING OUT THE INVENTION

Figure 1:
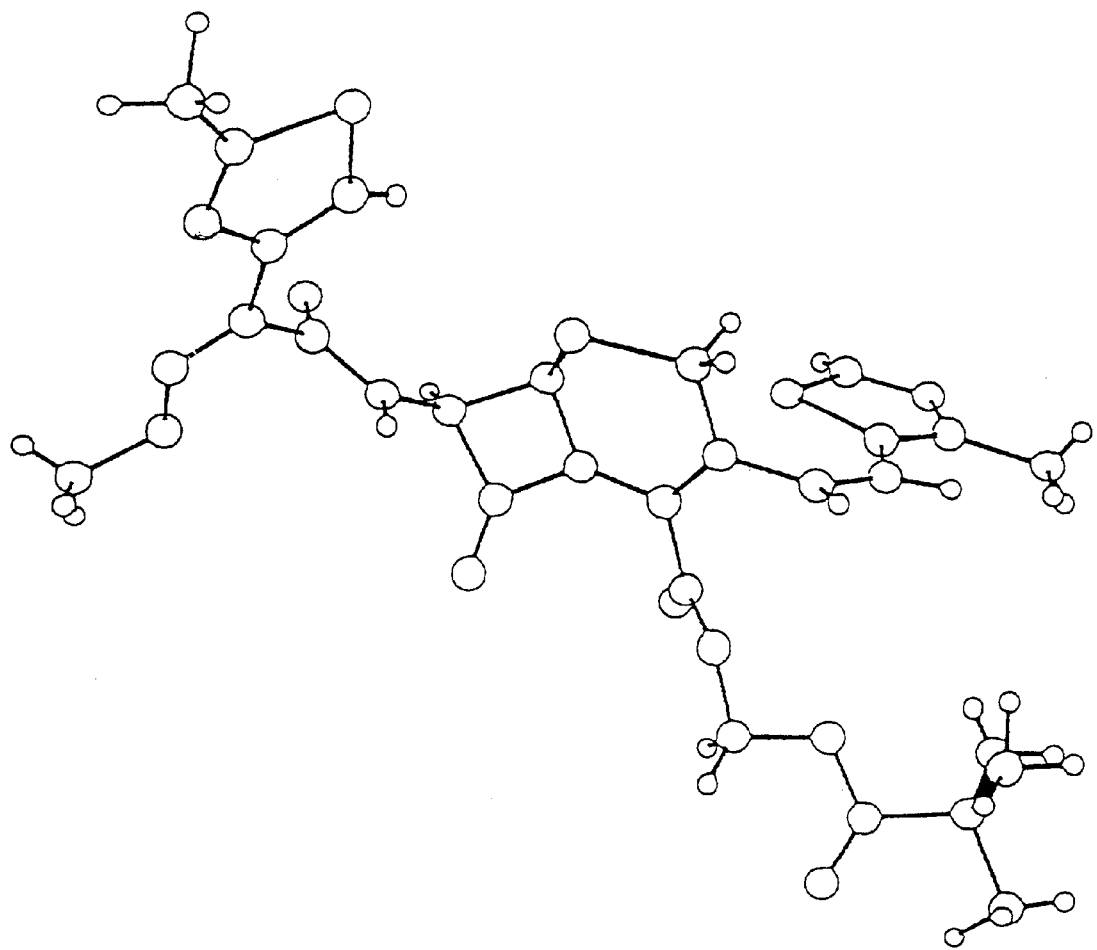
FIG. 1 depicts such a molecular conformation or steric structure of the crystalline Cefditoren pivoxyl of this invention, which has been elucidated from analysis of the crystal structure of single crystal by X-ray single-crystal diffractometer.

The production of the crystalline Cefditoren pivoxyl by the new processess of this invention is now illustrated with reference to the following Examples 1 to 9, to which this invention is not limited. Examples 1–3 are illustrative examples of carrying out the process according to the second aspect of this invention. Example 4 is an illustrative example of carrying out the process according to the process according to the third aspect of this invention. Examples 5 to 9 are illustrative examples of carrying out the process according to the fourth aspect of this invention.

EXAMPLE 1

An amorphous substance (10 g) of Cefditoren pivoxyl, namely 7-[(Z)-2-(2-aminothiazol-4-yl)-2-methoxyiminoacetamido]-3-[(Z)-2-(4-methylthiazol-5-yl)-ethenyl]-3-cephem-4-carboxylic acid pivaloyloxymethyl ester, was dissolved in ethyl acetate (400 ml) at room temperature (at 10° C.). The resulting solution containing the dissolved Cefditoren pivoxyl at a concentration of 25 mg/ml of ethyl acetate was then mixed with anhydrous ethanol (60 m) at a temperature of 5° C. or below, to prepare a solution containing 217 mg/ml of Cefditoren pivoxyl in the mixture of ethyl acetate and ethanol (totally 460 ml). This solution was concentrated to a volume of 80 ml by evaporation of ethyl acetate and ethanol under a reduced pressure of 20 Torr (in guage), with keeping the temperature of said solution below 10° C.

The concentrated solution so obtained had a concentration of 125 mg/ml of Cefditoren pivoxyl dissolved in a mixture of a larger proportion of ethanol and a smaller proportion of ethyl acetate. This concentrated solution was mixed with a further amount of anhydrous ethanol (80 ml) below 10° C., to prepare a solution containing 62.5 mg/ml of Cefditoren pivoxyl dissolved in a mixed solvent comprising a major proportion of ethanol and a minor proportion of ethyl acetate. The latter solution was then concentrated to a volume of 80 ml by evaporation of the solvents under a reduced pressure of 20 Torr, with keeping the temperature of the solution at a temperature of not higher than 10° C. In this way, there was afforded a concentrated solution containing 125 mg/ml of Cefditoren pivoxyl in ethanol as the substantially sole solvent present in said solution.

The thus obtained solution containing 125 mg/ml of Cefditoren pivoxyl in anhydrous ethanol was admixed with water (140 ml) at a temperature of not higher than 10° C., with allowing Cefditoren pivoxyl to deposit as crystalline particles in the resulting admixture. The resulting admixture containing the deposited Cefditoren pivoxyl therein was agitated overnight at the same temperature as above (namely, below 10° C.), so that the Cefditoren pivoxyl undergone a complete crystallization. The crystals as formed were separated from the remaining solution by filtration and then dried under a reduced pressure, yielding pale yellow crystals (9.5 g) of Cefditoren pivoxyl at a purity of 98%.

Figure 2:
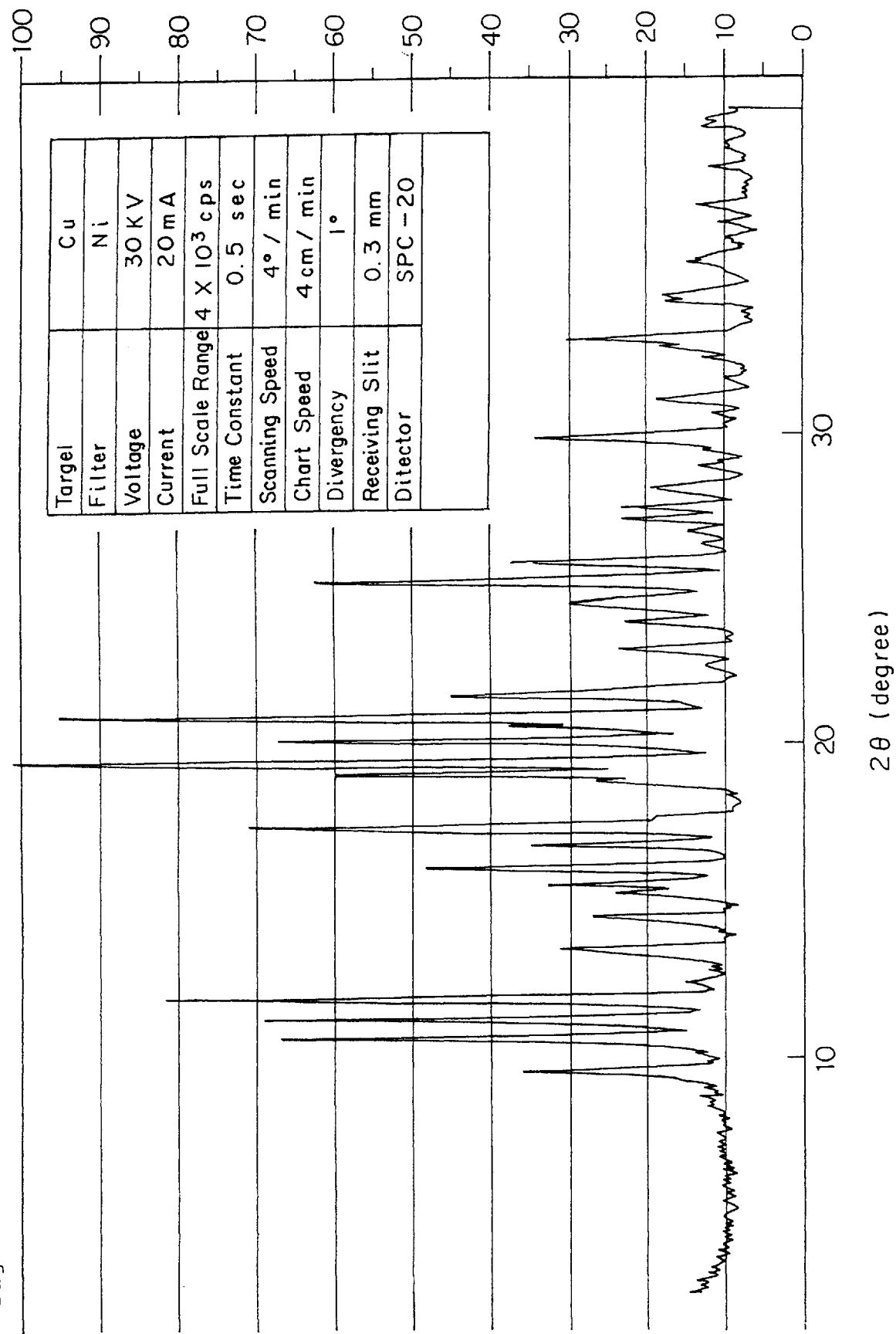
FIG. 2 shows a pattern of X-ray powder diffraction data of a crystalline substance of Cefditoren pivoxyl which was obtained in Example 1 given hereinafter according to this invention.

FIG. 2 of the accompanying drawings shows a pattern of such X-ray powder diffraction data of the above crystalline product of Cefditoren pivoxyl obtained in this Example 1, which was measured using an X-ray powder diffractometer (Model, Geiger-Flex 2027, an apparatus supplied from Rigaku-Denki Co., Ltd, Japan) with CuK-α beam at a voltage of 40 kilo-volts and an electric current of 30 milli-amperes. The pattern of FIG. 2 reveals that the Cefditoren pivoxyl product of this Example 1 w as in the crystalline form.

Figure 3:
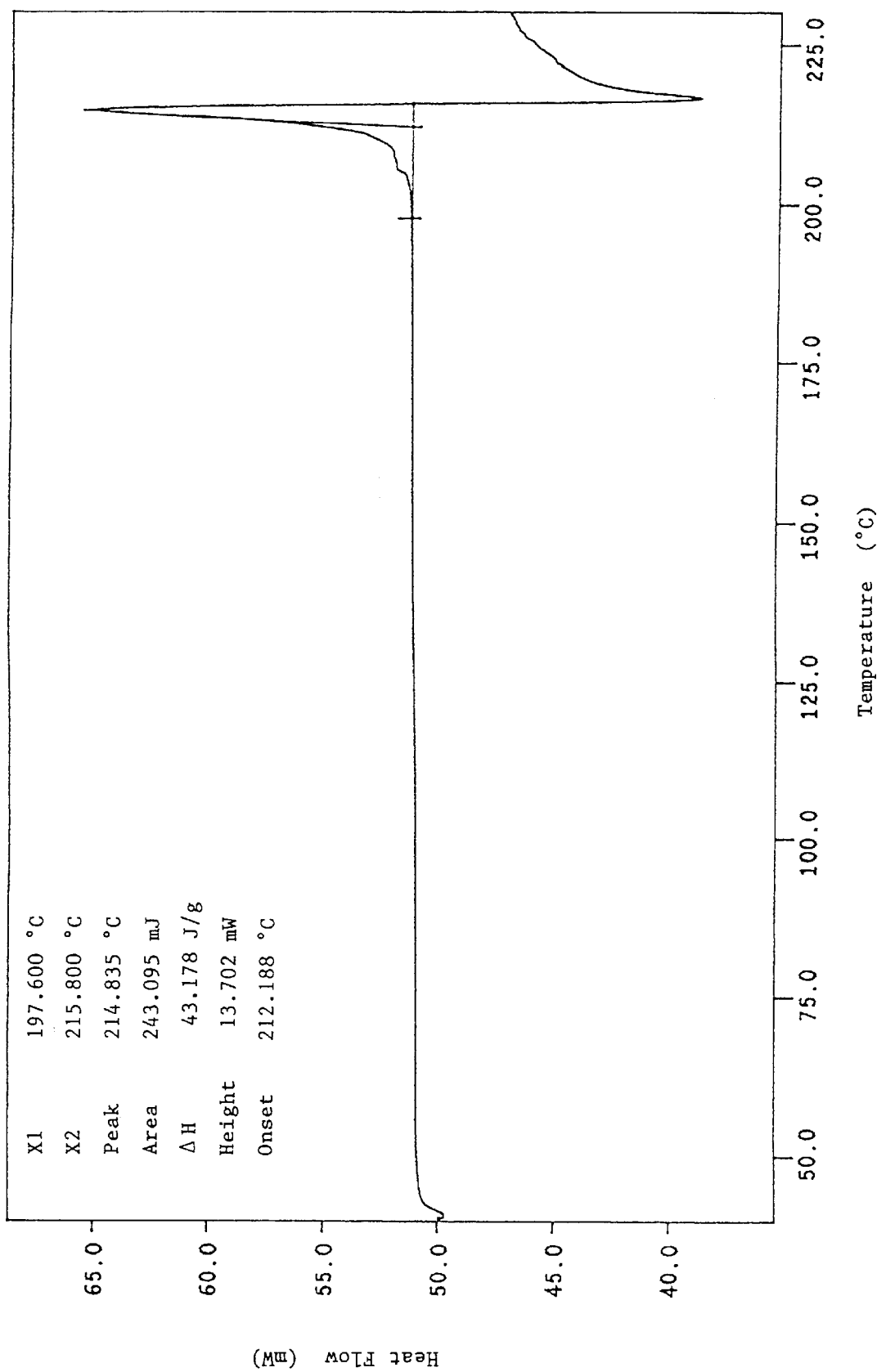
FIG. 3 shows such a curve of the heat flow vis. temperature (° C.), which was determined by testing the crystalline Cefditoren pivoxyl substance of Example 1 with a differential scanning calorimeter.

FIG. 3 of the accompaning drawings shows such a curve of the heat flow (in milli-Watts) vis. temperature (° C.) of the above crystalline Cefditoren pivoxyl product of Example 1, which was determined with a differential scanning calorimeter (an apparatus manufactured by Perkin-Elmer Co. Ltd., U.S.A.) at a rate of elevation of temperature of 10° C. per minute. The curve of FIG. 3 shows that a peak of the thermal absorption appeared at 214.835° C., indicating that the crystalline Cefditoren pivoxyl product of this Example 1 had a melting point of 214.8° C. with decomposition.

Such angles of the diffraction in the X-ray powder diffraction data of FIG. 2 at which the diffraction peaks are exhibited, as well as relative intensities of these diffraction peaks are tabulated in Table 4 below. The relative intensities of the diffraction peaks were evaluated as assumed that the value of the intensity of a maximum diffraction peak is amounting to 1000.

TABLE 4

Value of the diffraction angle exhibiting the diffraction peaks in the X-ray powder diffraction data shown in FIG. 2, and values of the relative intensities of the diffraction peaks

| Diffraction angle of 2 θ (degree) | Relative intensity of diffraction peak | Diffraction angle of 2 θ (degree) | Relative intensity of diffraction peak |
|---|---|---|---|
| 9.7 | 360 | 20.8 | 950 |
| 10.8 | 670 | 21.5 | 450 |
| 11.4 | 690 | 23.0 | 230 |
| 12.1 | 780 | 23.8 | 230 |
| 13.6 | 320 | 24.5 | 300 |
| 14.6 | 270 | 25.2 | 620 |
| 15.4 | 240 | 25.7 | 370 |
| 15.6 | 330 | 27.2 | 230 |
| 16.2 | 490 | 27.6 | 230 |
| 16.8 | 350 | 28.2 | 190 |
| 17.4 | 710 | 29.9 | 340 |
| 19.0 | 600 | 31.1 | 190 |
| 19.5 | 1000 | 33.0 | 300 |
| 20.1 | 670 | | |

Further, single crystals were taken from the crystalline Cefditoren pivoxyl product of this Example 1 and the crystallographic features of the single crystal were measured by an X-ray single-crystal diffractometer (Model, AFC-5R, manufactured by Rigaku-Denki Co. Ltd., Japan). The single crystal had the orthorhombic form and had a density of 1.22 g/cm$^3$ as measured by a conventional method. The measurement results obtained are summarized in Table 1 given hereinbefore.

EXAMPLES 2–3

The procedures of Example 1 above were repeated by using methanol in place of ethanol.

The procedures of Example 1 were again repeated by using iso-propanol in place of ethanol.

In these two runs of the experiments, there were obtained pale yellow crystals of Cefditoren pivoxyl in yields of 7.6 g and 7.8 g, respectively. The two crop products of the crystalline Cefditoren pivoxyl were found to be of the orthorhombic form and have a purity of 98% and a purity of 97%, respectively.

EXAMPLE 4

An amorphous substance (10 g) of Cefditoren pivoxyl was dissolved in ethyl acetate (400 ml) at room temperature (at 10° C.). The resulting solution containing the dissolved Cefditoren pivoxyl at a concentration of 25 mg/ml in ethyl acetate was then added with 0.02 g of a previously prepared crystalline substance of Cefditoren pivoxyl obtained in Example 1, as the seed crystal.

The solution of Cefditoren pivoxyl in ethyl acetate containing the seed crystal added was incubated at 10° C. for 40 hours under mechanical agitation. After this incubation, this solution was concentrated to a volume of 40 ml under a reduced pressure of 20 Torr, with keeping the temperature of the solution below 10° C. The concentrated solution so obtained contained 250 mg/ml of the dissolved Cefditoren pivoxyl in ethyl acetate along with the seed crystal.

This concentrated solution in ethyl acetate was then mixed with ethanol (60 ml) to prepare a solution containing 100 mg/ml of Cefditoren pivoxyl in the mixture of ethyl acetate and ethanol, along with the seed crystal. The latter solution was again concentrated to a volume of 40 ml under a reduced pressure of 20 Torr, with keeping the temperature of the solution below 10° C., so that there was formed a concentrated solution containing 250 mg/ml of Cefditoren pivoxyl dissolved in ethanol as a substantially sole solvent and containing the seed crystal therein.

The concentrated solution so obtained was admixed with water (140 ml) at a temperature of not higher than 10° C., thereby to make crystalline solid particles of Cefditoren pivoxyl to start to deposit in the resulting admixture. This admixture was agitated overnight at a temperature of not higher than 10° C. for the purpose that the crystalline Cefditoren pivoxyl was made to be deposited from the solution to a complete extent. The deposited crystalline particles of Cefditoren pivoxyl were separated from the remaining solution (the liquid phase) by filtration and then dried under a reduced pressure, yielding 9.5 g of Cefditoren pivoxyl as pale yellow crystals.

Figure 4:
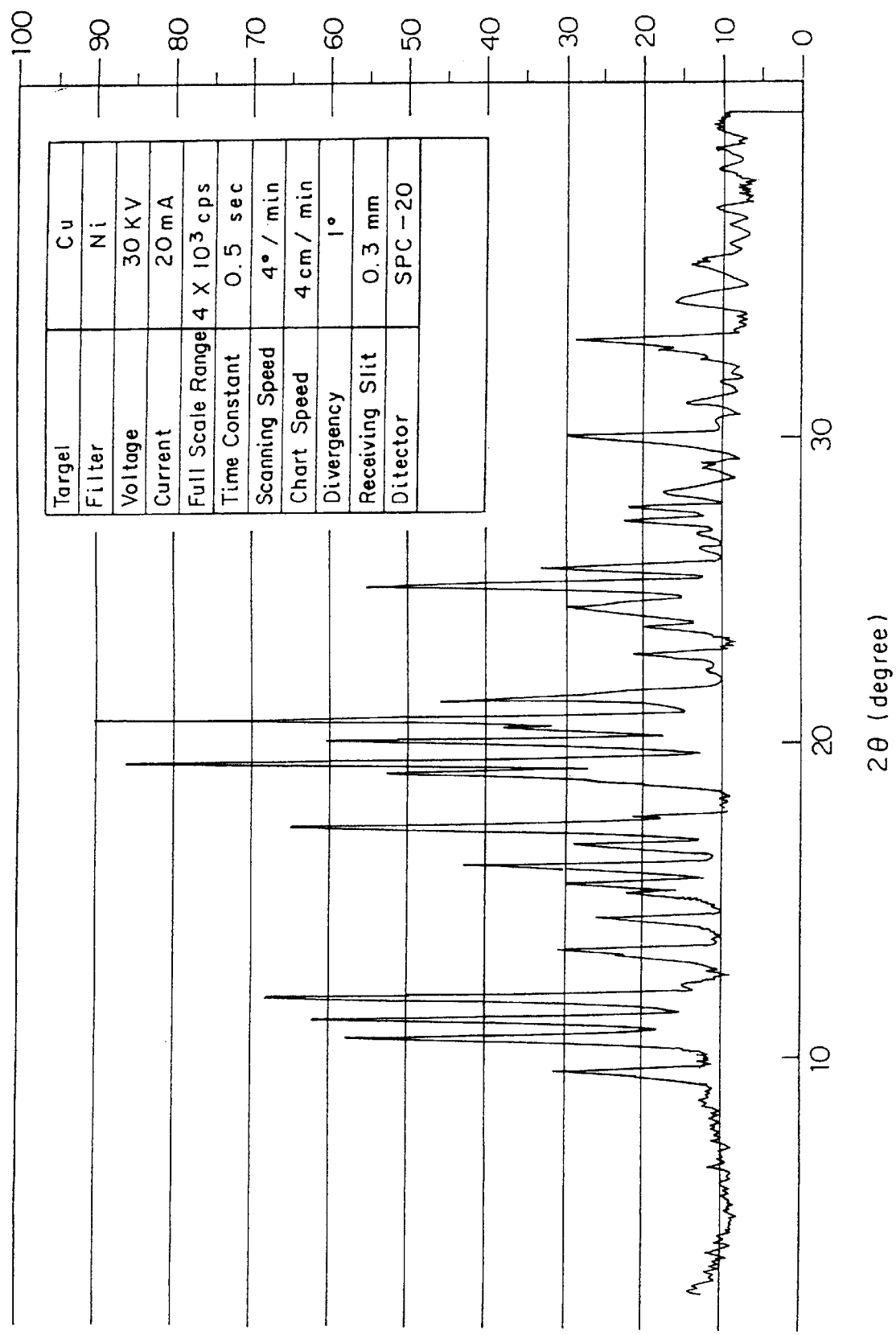
FIG. 4 shows a pattern of X-ray powder diffraction data of a crystalline substance of Cefditoren pivoxyl which was obtained in Example 4 according to this invention.

FIG. 4 of the accompanying drawings shows a pattern of such X-ray powder diffraction data of the crystalline Cefditoren pivoxyl product obtained in this Example 4, which were measured in the same manner as in Example 1.

Figure 5:
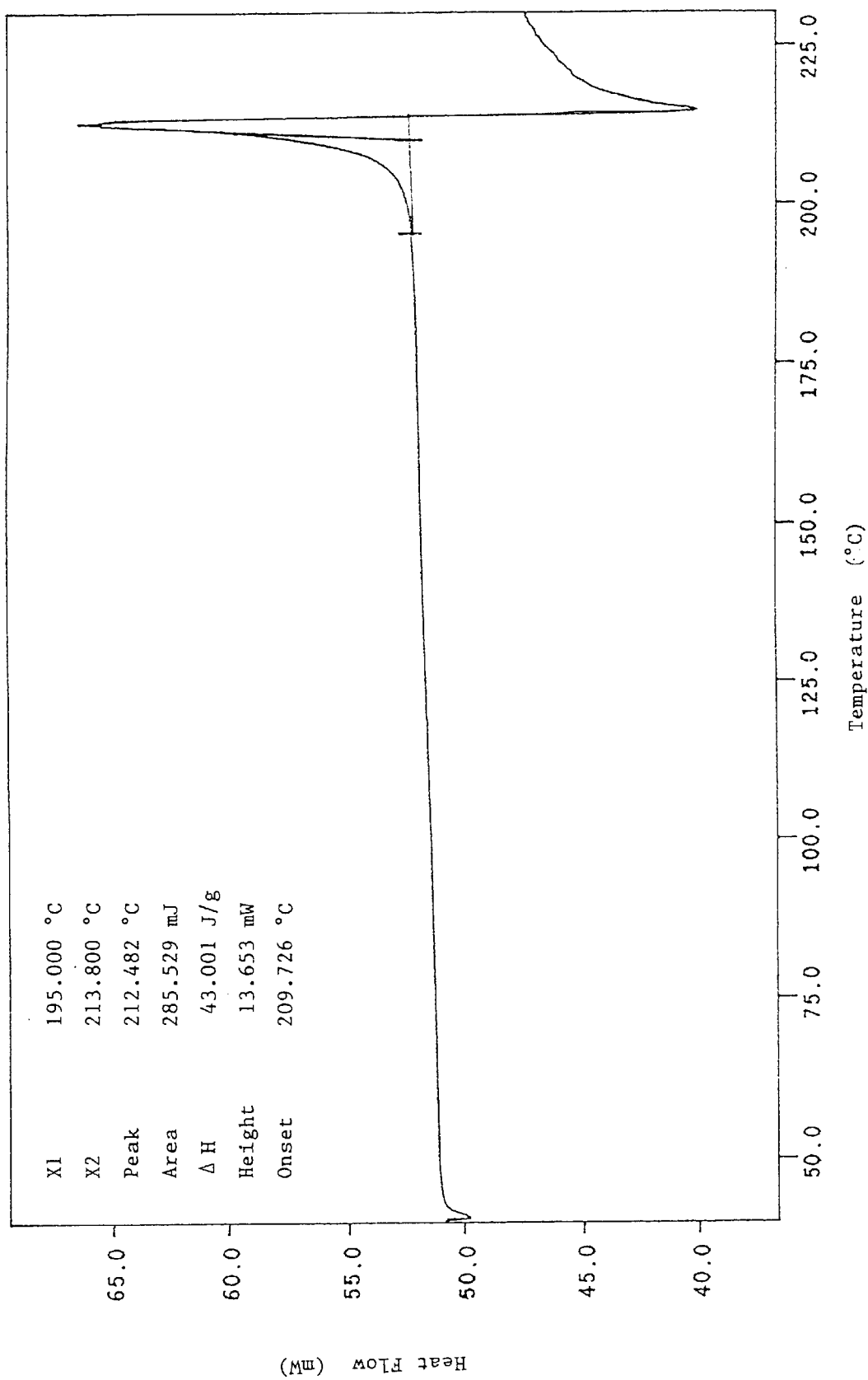
FIG. 5 shows such a curve of the heat flow vis. temperature (° C.), which was determined by testing the crystalline Cefditoren pivoxyl substance of Example 4 with the differential scanning calorimeter.

FIG. 5 of the accompanying drawings shows such a curve of the heat flow (milli-Watts) vis. temperature (° C.) of the crystalline Cefditoren pivoxyl product of Example 4, which was measured determined by testing this product with the differential scanning calorimeter in the same manner as in Example 1. The curve of FIG. 5 shows that a peak of the thermal absorption appeared at a temperature of 212.482° C., indicating that the crystalline Cefditoren pivoxyl product of Example 4 had a melting point of 212.4° C. with decomposition.

The crystalline Cefditoren pivoxyl product of this Example 4 had a purity of 98.0%, as analyzed by a liquid chromatography on a reverse phase silica gel column.

EXAMPLE 5

The amorphous substance (10 g) of Cefditoren pivoxyl was dissolved in ethyl acetate (400 ml) to prepare a solution containing 25 mg/ml of Cefditoren pivoxyl dissolved in ethyl acetate. To this solution was added seed crystal (0.02 g) of Cefditoren pivoxyl which had been prepared previously. The resulting solution of Cefditoren pivoxyl containing the seed crystal added was then agitated at room temperature (at 10° C.) under ultra-sonic irradiation. During this agitation, the crystallization of Cefditoren pivoxyl proceeded. The crystals as formed were separated from the remaining liquid phase of the solution by filtration and dried under a reduced pressure to afford pale yellow colored crystals of Cefditoren pivoxyl in a yield of 7 g.

The crystalline Cefditoren pivoxyl product obtained in this Example had a purity of 98% as analyzed by the liquid chromatography.

Further, this crystalline Cefditoren pivoxyl product showed such a pattern of the X-ray powder diffraction data and such a curve of the heat flow vis. temperature (° C.), which are same as those shown in FIGS. 4 and 5 of the accompanying drawings, respectively.

EXAMPLE 6

The procedures of Example 5 were repeated with using acetone in place of ethyl acetate. A crystalline substance of Cefditoren pivoxyl was obtained in a yield of 6.5 g and at a purity of 97.8%.

Figure 6:
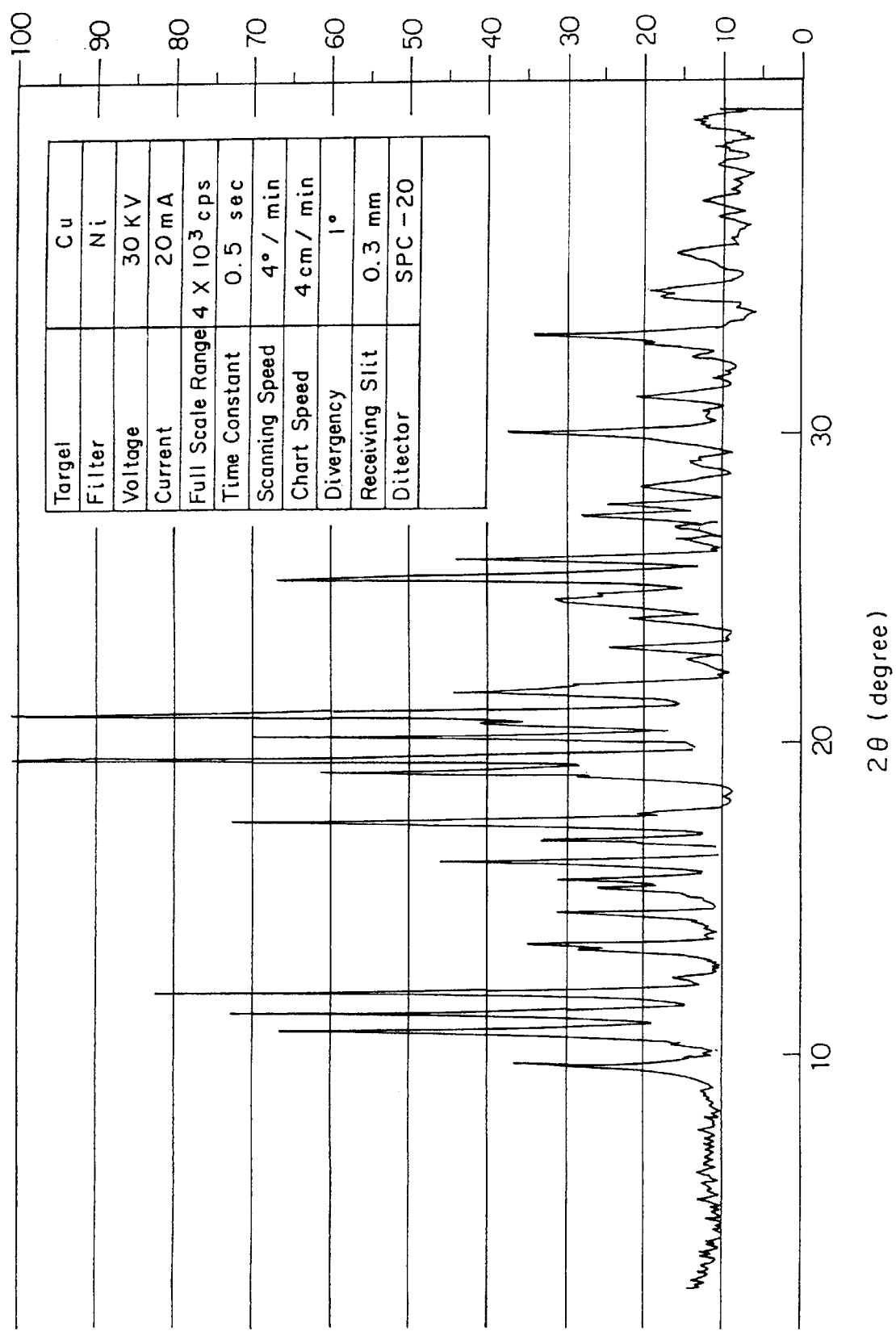
FIG. 6 shows a pattern of X-ray powder diffraction data of the crystalline substance of Cefditoren pivoxyl which was obtained in Example 6 according to this invention.
Figure 7:
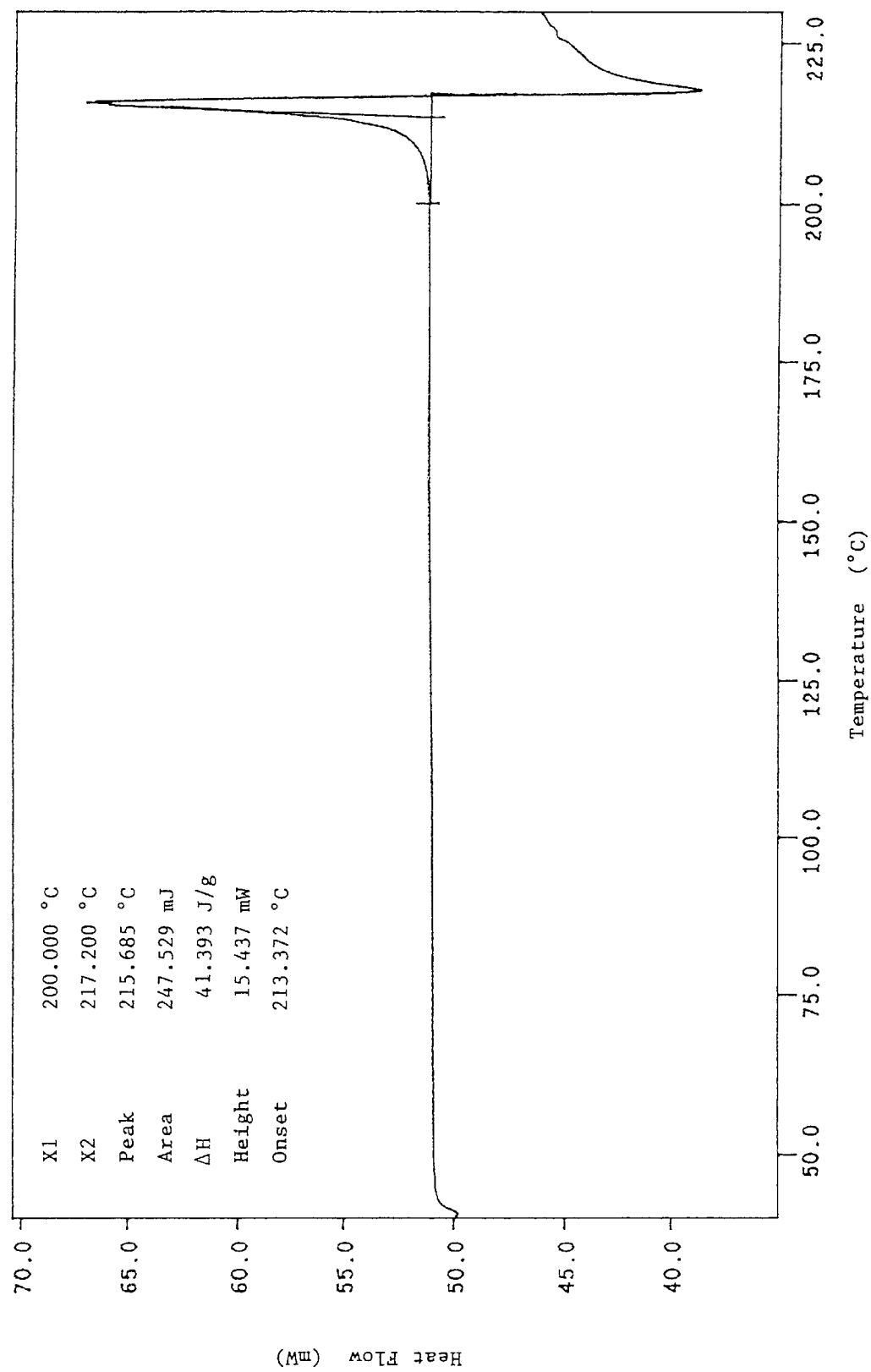
FIG. 7 shows such a curve of the heat flow vis. temperature (° C.), which was determined by testing the crystalline Cefditoren pivoxyl substance of Example 6 with the differential scanning calorimeter.

The X-ray powder diffraction data of this crystalline Cefditoren pivoxyl product were measured in the same way as in Example 1 and is shown in FIG. 6 of the accompanying drawings. Further, this crystalline Cefditoren pivoxyl product was tested with the differential scanning calorimeter in the same manner as in Example 1, and the resultant curve of the heat flow vis. temperature as determined of this product is shown in FIG. 7 of the accompaning drawings. The curve of FIG. 7 indicates that this crystalline Cefditoren pivoxyl product had a melting point of 215.6° C. with decomposition.

EXAMPLE 7

The procedure of Example 5 were repeated with using methanol in place of ethyl acetate. A crystalline substance of Cefditoren pivoxyl was obtained in a yield of 8 g and at a purity of 97.5%.

Figure 8:
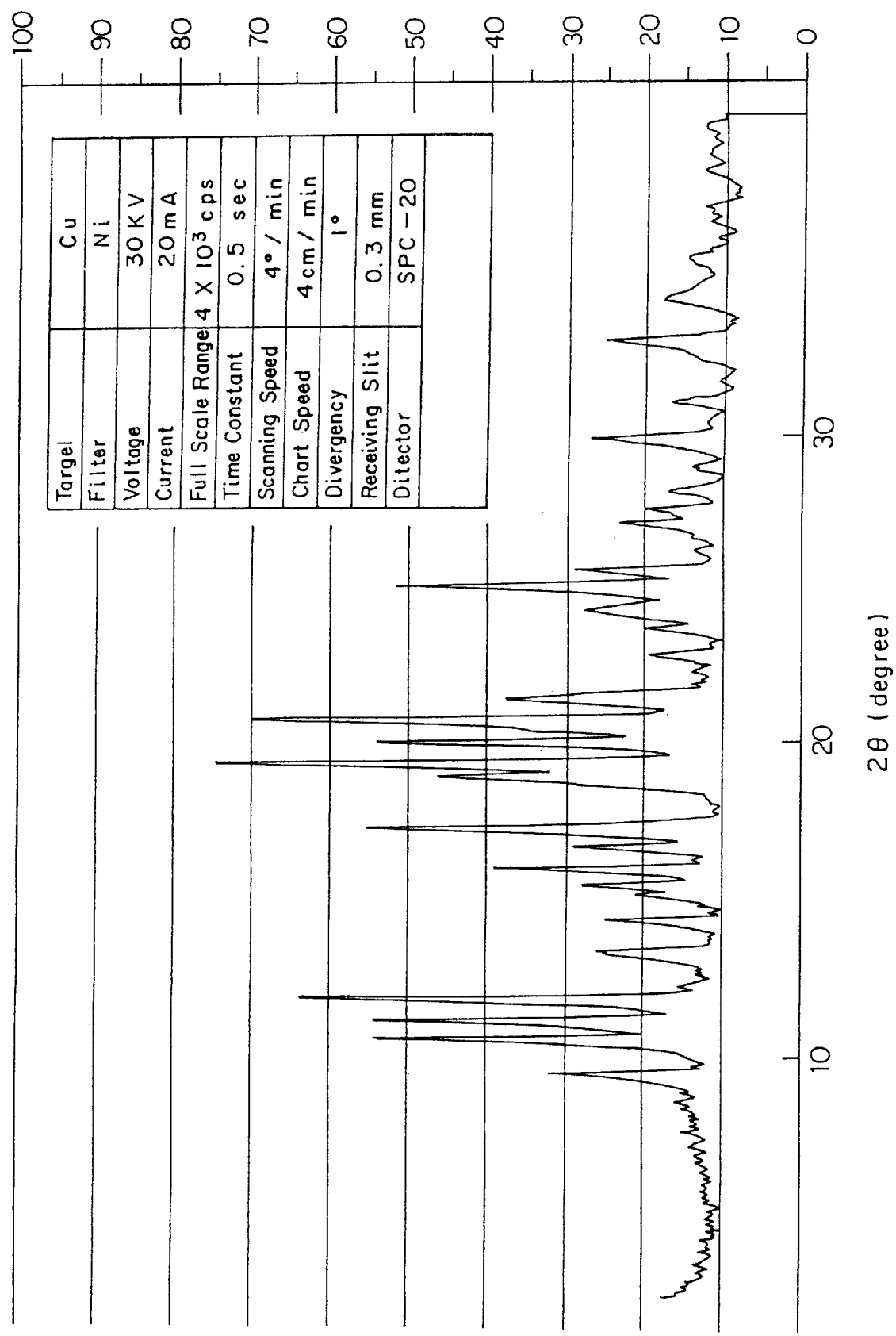
FIG. 8 shows a pattern of X-ray powder diffraction data of a crystalline substance of Cefditoren pivoxyl which was obtained in Example 7 according to this invention.
Figure 9:
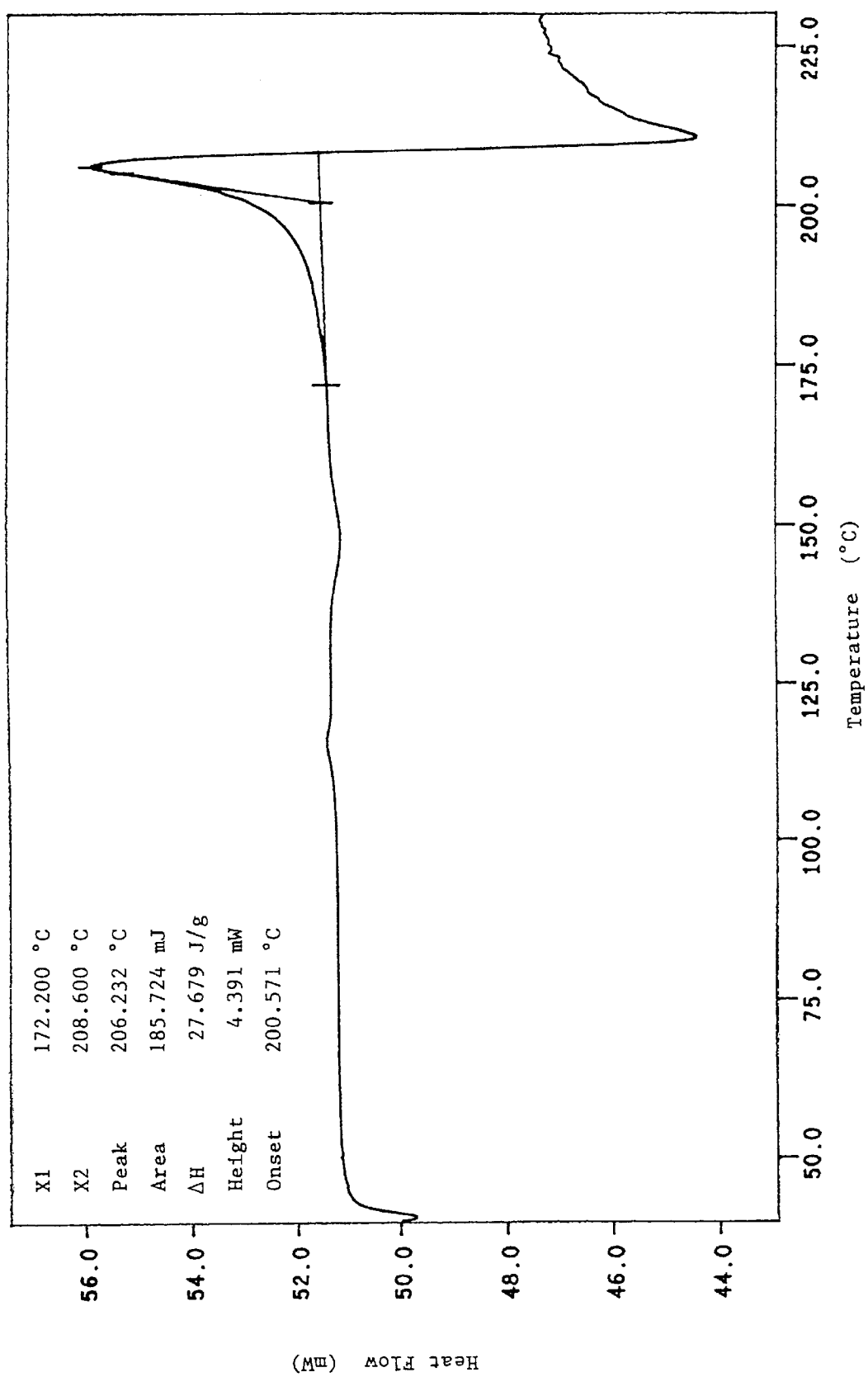
FIG. 9 shows such a curve of the heat flow vis. temperature (° C.), which was determined by testing the crystalline Cefditoren pivoxyl substance of Example 7.

The X-ray powder diffraction data of this crystalline Cefditoren pivoxyl product were measured in the same manner as in Example 1 and is shown in FIG. 8 of the accompanying drawings. Further, this crystalline Cefditoren pivoxyl product was tested with the differential scanning calorimeter in the same manner as in Example 1, and the resultant curve of the heat flow vis. temperature as determined of this product is shown in FIG. 9 of the accompanying drawings. The curve of FIG. 9 indicates that this crystalline Cefditoren pivoxyl product had a melting point of 206.2° C. with decomposition.

EXAMPLE 8

The procedures of Example 5 were repeated with using methylene chloride in place of ethyl acetate. A crystalline substance of Cefditoren pivoxyl was obtained in a yield of 6 g and at a purity of 97%.

Figure 10:
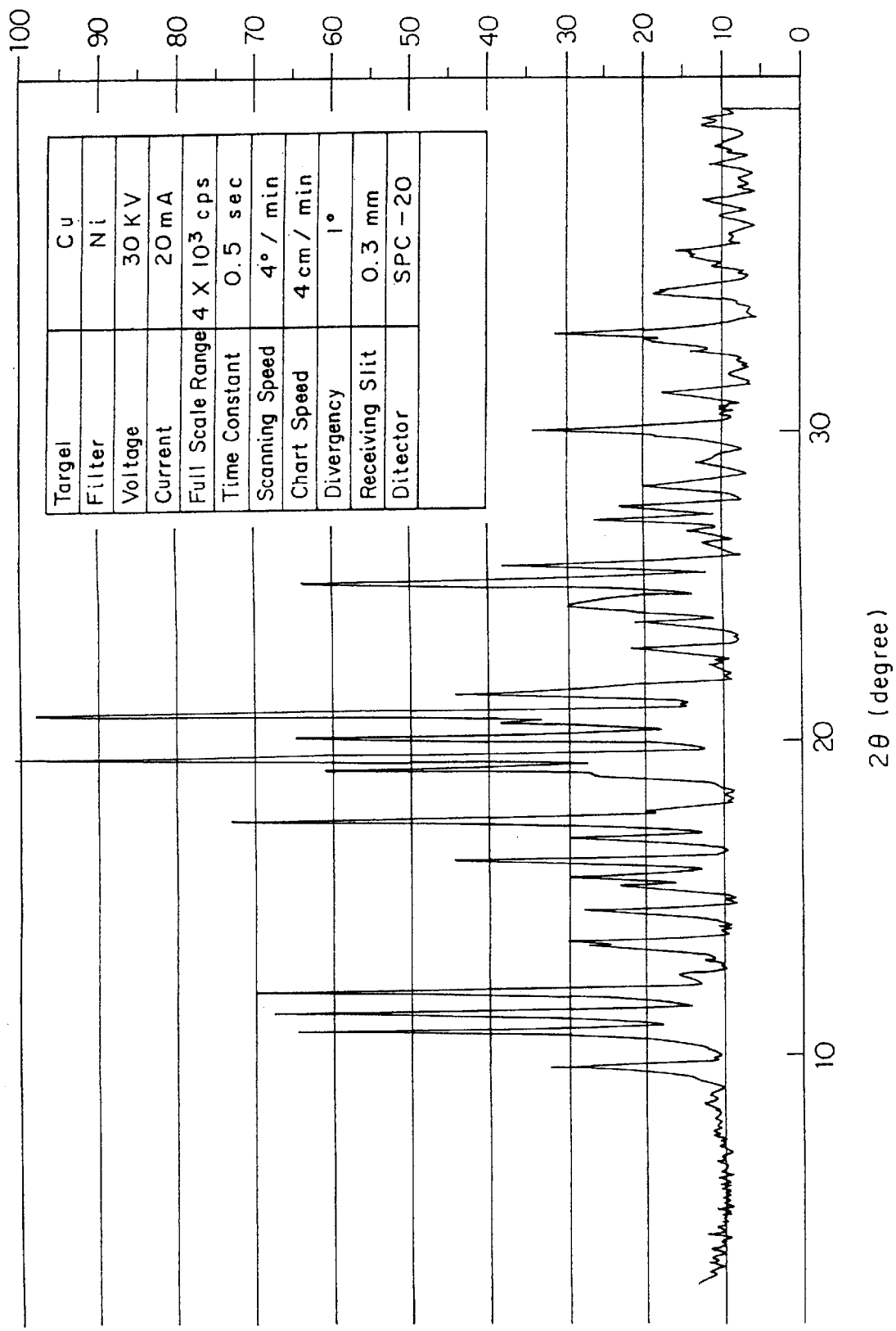
FIG. 10 shows a pattern of X-ray powder diffraction data of a crystalline substance of Cefditoren pivoxyl which was obtained in Example 8 given hereinafter according to this invention.
Figure 11:
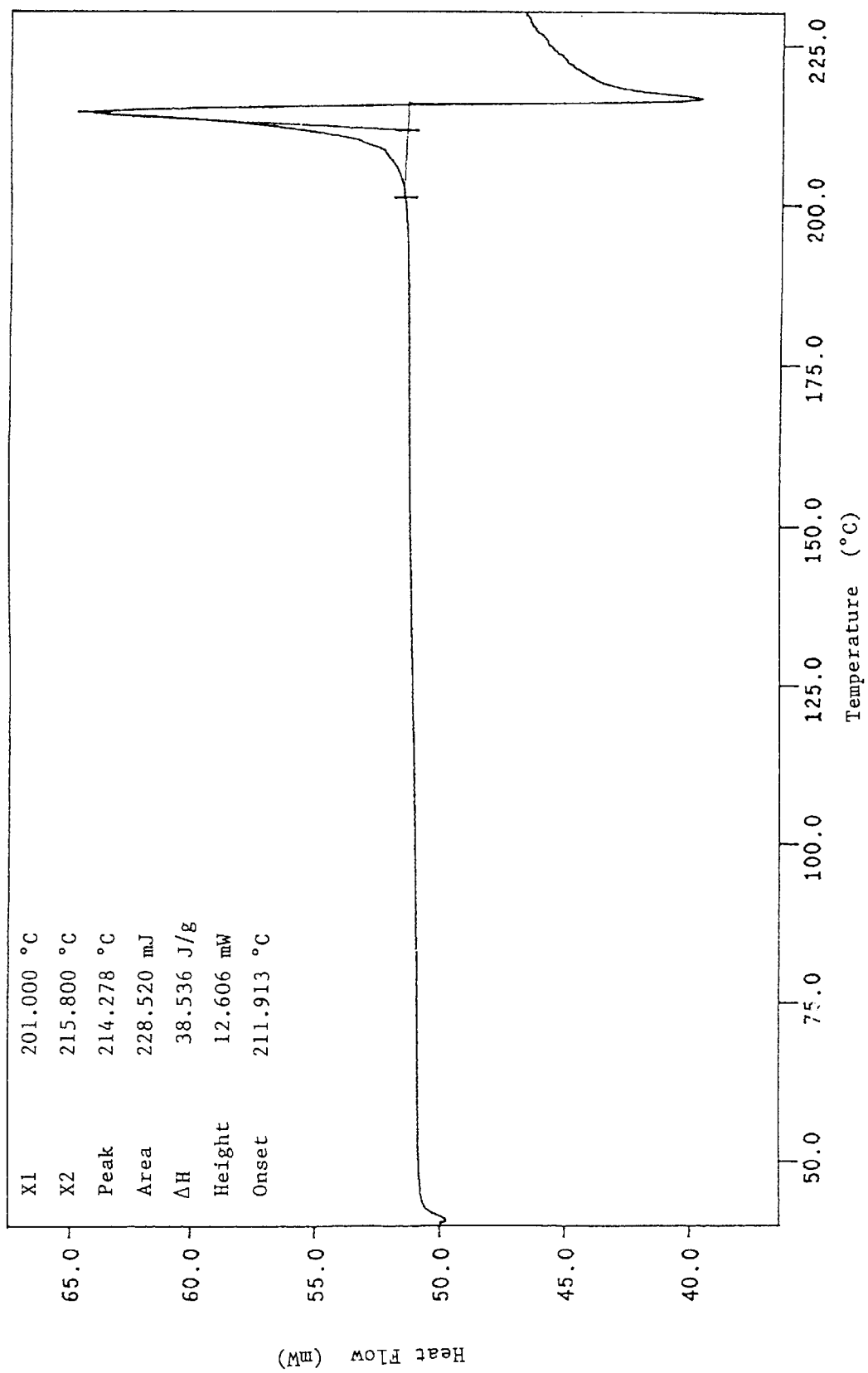
FIG. 11 shows such a curve of the heat flow vis. temperature (° C.), which was determined by testing the crystalline Cefditoren pivoxyl substance of Example 8 with a differential scanning calorimeter.

The X-ray powder diffraction data of this crystalline Cefditoren pivoxyl product were measured in the same way as in Example 1 and is shown in FIG. 10 of the accompanying drawings. Further, this crystalline Cefditoren pivoxyl product was tested with the differential scanning calorimeter in the same manner as in Example 1, and the resultant curve of the heat flow vis. temperature as determined of this product is shown in FIG. 11 of the accompaning drawings. The curve of FIG. 11 indicates that this crystalline Cefditoren pivoxyl product had a melting point of 214.3° C. with decomposition.

EXAMPLE 9

The procedure of Example 5 were repeated with using acetonitorile in place of ethyl acetate. A crystalline substance of Cefditoren pivoxyl was obtained in a yield of 7 g and at a purity of 97.5%.

Figure 12:
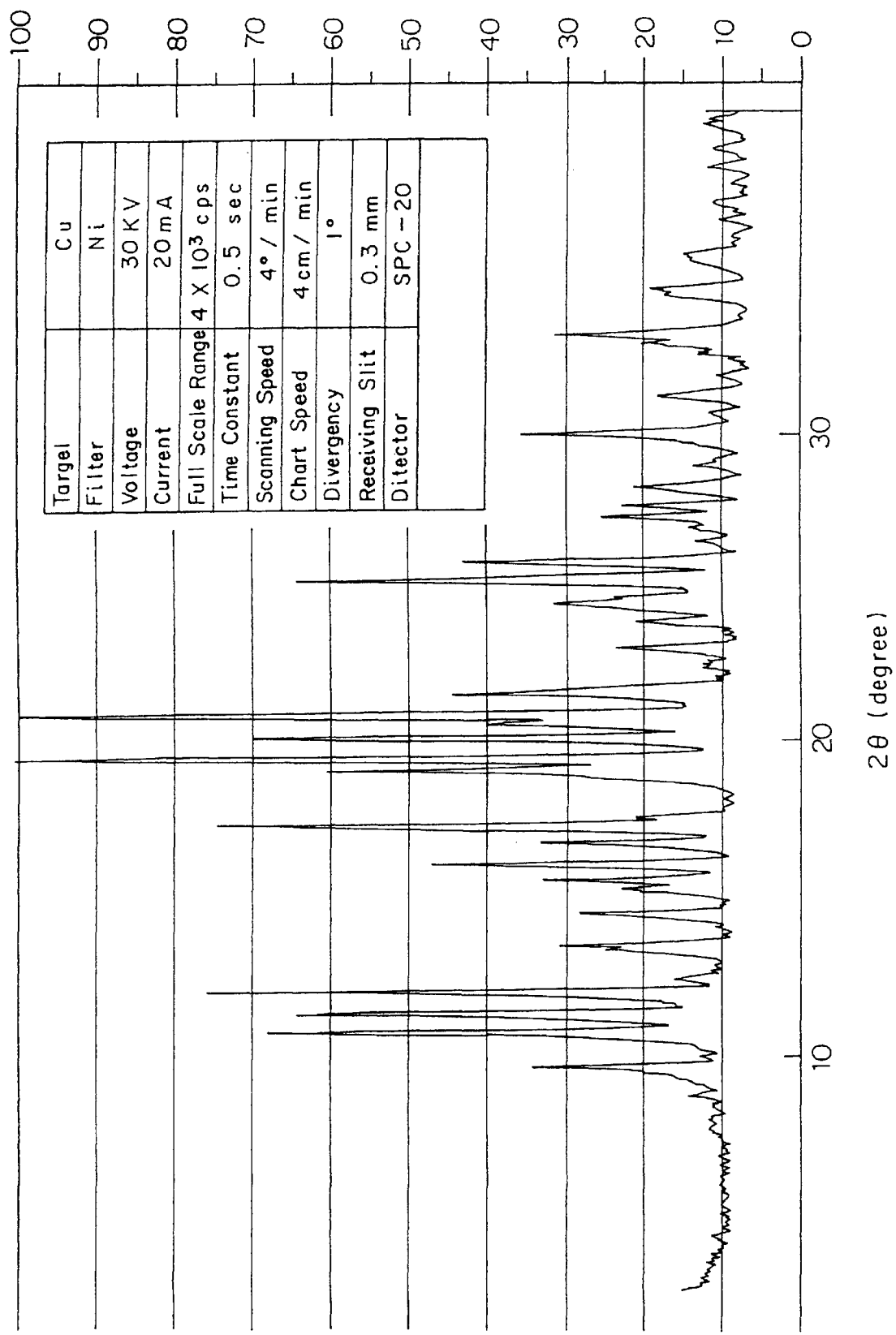
FIG. 12 shows a pattern of X-ray powder diffraction data of a crystalline substance of Cefditoren pivoxyl which was obtained in Example 9 according to this invention.
Figure 13:
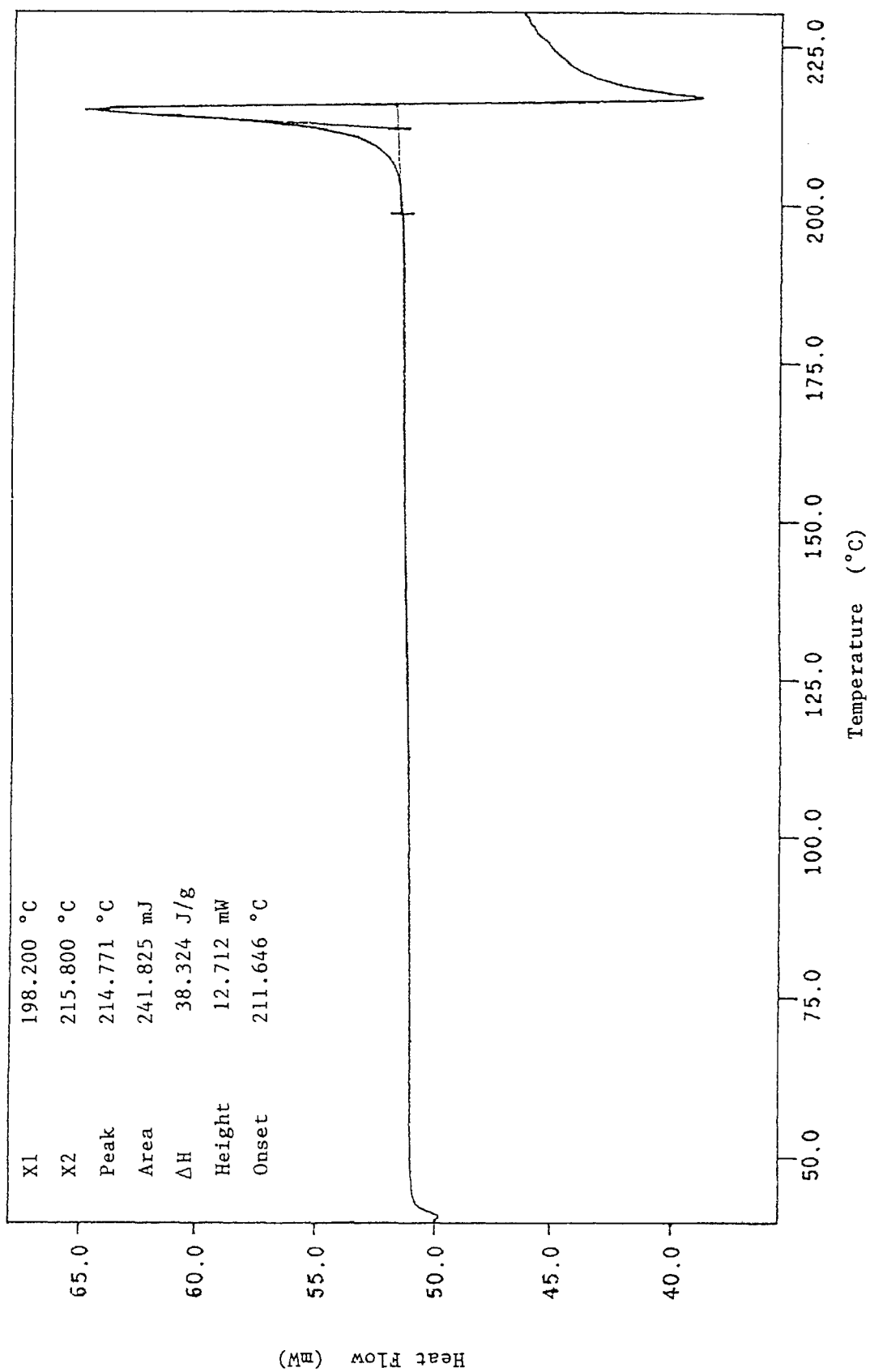
FIG. 13 shows such a curve of the heat flow vis. temperature (° C.), which was determined by testing the crystalline Cefditoren pivoxyl substance of Example 9 with the differential scanning calorimeter.

The X-ray powder diffraction data of this crystalline Cefditoren pivoxyl product were measured in the same manner as in Example 1 and is shown in FIG. 12 of the accompanying drawings. Further, this crystalline Cefditoren pivoxyl product was tested with the differential scanning calorimeter in the same manner as in Example 1, and the resultant curve of the heat flow vis. temperature as determined of this product is shown in FIG. 13 of the accompanying drawings. The curve of FIG. 13 indicates that this crystalline Cefditoren pivoxyl product had a melting point of 214.8° C. with decomposition.

Industrial Applicability

As described hereinbefore, according to this invention it has been made feasible to obtain, as a novel substance, a crystalline substance of Cefditoren pivoxyl which has a higher purity than and has a superior thermal stability on storage to the known, amorphous substance of Cefditoren pivoxyl. The new, crystalline substance of Cefditoren pivoxyl obtained according to this invention is advantageous to be utilized as a bulk material which is used to prepeare an orally administrable antibiotic drug having a broad antibacterial spectrum. Further, there have been provided such new processes for preparing the crystalline substance of Cefditoren pivoxyl, which may be carried out in an efficient way on a commercial scale.

What is claimed is:

1. A crystalline form of Cefditoren pivoxyl having orthorhombic form characterized in that an X-ray powder diffractometer data of said crystalline substance of Cefditoren pivoxyl shows peaks at the following diffraction angles:

approximately 9.7 degree, approximately 10.8 degree, approximately 11.4 degree, approximately 12.1 degree, approximately 13.6 degree, approximately 15.6 degree, approximately 16.2 degree, approximately 17.4 degree, approximately 19.0 degree, approximately 19.5 degree, approximately 20.1 degree, approximately 20.8 degree, approximately 21.5 degree, approximately 25.2 degree, approximately 29.9 degree, approximately 33.0 degree, and that the single crystal of said crystalline form has substantially the following crystallographic features:

Crystalline system: Orthorhombic form
Lattice constants: a=14.026 Å, b=18.438 Å, c=11.815 Å, $\alpha=90°$, $\beta=90°$, $\gamma=90°$
Space group: $P2_1 P2_1 P2_1$,
Number of molecules within a single unit lattice: 4
Lattice capacity: 3055 Å$^3$ Density: 1.22 g/cm$^3$ on average,
R value: 4%.

2. A process for the preparation of a crystalline form of Cefditoren pivoxyl having the orthorhombic form, which comprises conducting successively the following first to seventh steps:

in a first step, dissolving an amorphous form of Cefditoren pivoxyl in an anhydrous, first organic solvent in which Cefditoren pivoxyl is much more soluble than in an alkanol containing 1 to 5 carbon atoms and which is miscible with said alkanol, thereby to obtain a solution containing 10 mg to 50 mg of the dissolved Cefditoren pivoxyl per 1 ml of the resulting solution of Cefditoren pivoxyl in the first organic solvent, in a second step, mixing the resulting solution of Cefditoren pivoxyl in the first organic solvent with an anhydrous alkanol containing 1 to 5 carbon atoms as a second organic solvent in such a proportion thereof necessary to reduce the concentration of the Cefditoren pivoxyl dissolved in the resulting mixture of said solution of Cefidtoren pivoxyl with the second organic solvent, to a concentration of 5 mg to 40 mg of the disslved Cefditoren pivoxyl per 1 ml of said resulting mixture, in a third step, concentrating the resulting solution of Cefditoren pivoxyl in the mixed first and second organic solvents as obtained in the second step, at a temperature of –5° C. to 15° C. by evaporation of the organic solvents from said solution under a reduced pressure, to give a concentrated solution containing 50 mg/ml to 250 mg/ml of the dissolved Cefditoren pivoxyl, in a fourth step, mixing the concentrated solution so obtained in the third step with a further volume of an alkanol of 1 to 5 carbon atoms used as the second organic solvent in such a proportion thereof necessary to reduce the concentration of the Cefditoren pivoxyl dissolved in the resulting mixture of said concentrated solution with the further volume of the alkanol, to a concentration of 25 mg to 125 mg of the dissolved Cefditoren pivoxyl per 1 ml of said resulting mixture, in a fifth step, concentrating the resulting solution of Cefidtoren pivoxyl so diluted with the further volume of the alkanol in the fourth step, at a temperature of –5° C. to 15° C. by evaporation of the solvents from said solution under a reduced pressure, to give a concentrated solution containing 50 mg/ml to 250 mg/ml of the Cefditoren pivoxyl dissolved in the solvent entirely or substantially entirely made of said alkanol, in a sixth step, agitating the above mentioned concentrated solution as obtained in the fifth step, at a temperature of 0° C. to 10° C. for a time sufficient to effect a complete crystallization of Cefditoren pivoxyl, and in a seventh step, separating and harvesting the crystalline Cefditoren pivoxyl from the remaining solution by filtration or centrifugation, followed by drying the harvested crystalline Cefditoren pivoxyl substance under a reduced pressure.

3. A process for the preparation of a crystalline form of Cefditoren pivoxyl having the orthorhombic form, which comprises conducting successively the following step (a) to step (i):

(a) providing a crystalline form of Cefditoren pivoxyl having the orthorhombic form, (b) placing the crystalline form of Cefditoren pivoxyl as a seed crystal in a solution containing 10 mg/ml to 50 mg/ml of Cefdiroren pivoxyl which has been prepared by dissolution of an amorphous form of Cefditoren pivoxyl in an anhydrous, first organic solvent which is chosen from ethylene glycol, propylene glycol, acetone, methyl ethyl ketone, methyl iso-butyl ketone, tetrahydrofuran, dioxane, acetonitile, a lower alkyl ester of acetic acid, methylene chloride and chloroform, as well as mixed solvents of two or more of them, (c) incubating the solution of Cefditoren pivoxyl in the first organic solvent and further containing therein the seed crystal of Cefditoren pivoxyl added in the above step (b), at a temperature of 0° C. to 50° C. for a time of 10 minutes to 48 hours, to make a crystalline form of Cefditoren pivoxyl to start to deposit from said solution, (d) concentrating the solution of Cefditoren pivoxyl with the seed crystal so incubated in the above step (c), at a temperature of −5° C. to 15° C. by evaporation of the first organic solvent therefrom under a reduced pressure, thereby to give a concentrated solution containing 50 mg/ml to 250 mg/ml of the dissolved Cefditoren pivoxyl and the seed crystal of Cefditoren pivoxyl remaining therein, (e) mixing the concentrated solution of Cefditoren pivoxyl containing the remaining seed crystal as obtained in the above step (d) with an anhydrous alkanol of 1 to 5 carbon atoms as the second organic solvent in a proportion thereof necessary to reduce the concentration of the dissolved Cefditoren pivoxyl to a concentration of 25 mg/ml to 125 mg/ml of the Cefditoren pivoxyl dissolved in the resulting mixture of said concentrated solution of Cefditoren pivoxyl with the alkanol which still contains the remaining seed crystal of Cefditoren pivoxyl, (f) concentrating the resulting mixture of the concentrated solution of Cefditoren pivoxyl with the alkanol as obtained in the above step (e), at a temperature of −5° C. to 15° C. by evaporation of the first organic solvent and the alkanol therefrom under a reduced pressure, thereby to give a concentrated solution containing the dissolved Cefditoren pivoxyl at its concentration of 50 mg/ml to 250 mg/ml and the remaining seed crystal of Cefditoren pivoxyl, (g) mixing the concentrated solution comprising the dissolved Cefditoren pivoxyl and the remaining seed crystal as obtained in the above step (f), with water of a volume of 1-fold to 20-folds greater than the volume of said concentrated solution of Cefditoren pivoxyl, at a temperature of 0° C. to 10° C., thereby to facilitate a crystalline substance of Cefditoren pivoxyl to deposit from the resulting mixture of said concentrated solution of Cefditoren pivoxyl with water, (h) agitating the resulting aqueous mixture of the solution containing the dissolved Cefditoren pivoxyl, water and the deposited crystalline substance of Cefditoren pivoxyl as obtained in the above step (g), at a temperature of 0° C. to 10° C., for a time of 20 hours to 40 hours, thereby to effect a complete crystallization of the Cefditoren pivoxyl, and (i) separating and harvesting the crystals from the remaining solution obtained in the above step (h), followed by drying the harvested crystals under a reduced pressure.

4. A process for the preparation of a crystalline form of Cefditoren pivoxyl having the orthorhombic form, which comprises consecutively conducting the following steps (i) to (iv):

(i) a step of providing a crystalline form of Cefditoren pivoxyl having the orthorhombic form, (ii) a step of placing the crystalline form of Cefditoren pivoxyl provided in the step (i), as a seed crystal in a solution of Cefditoren pivoxyl which has been prepared by dissolution of an amorphous substance of Cefditoren pivoxyl to a concentration of 10 mg/ml to 50 mg/ml in an anhydrous organic solvent chosen from ethylene glycol, propylene glycol, acetone, methyl ethyl ketone, methyl iso-butyl ketone, tetrahydrofuran, dioxane, acetonitile, a lower alkyl ester of acetic acid, methylene chloride, chloroform and mixed solvents of two or more of them, as well as methanol, ethanol, n-propanol, iso-propanol, n-butanol, iso-butanol, sec-butanol, tert-butanol, n-amyl alcohol, iso-amyl alcohol, sec-amyl alcohol, tert-amyl alcohol, and mixed solvents of two or more of them, (iii) a step of agitating the resulting mixture of the solution of Cefditoren pivoxyl in the organic solvent with the seed crystal of Cefditoren pivoxyl as obtained in the step (ii), at a temperature of not higher than 10° C., for a time sufficient to facilitate crystallization of the Cefditoren pivoxyl in the solution, and (iv) separating and harvesting the deposited crystalline substance of Cefditoren pivoxyl from the remaining solution by filtration or centrifugation, followed by drying the harvested crystals of Cefditoren pivoxyl under a reduced pressure.

5. A process according to claim 3, in which the solution of Cefditoren pivoxyl in the anhydrous first organic solvent to be added with the seed crystal of Cefditoren pivoxyl in the step (b) is such solution that has been prepared by dissolution of the amorphous substance of Cefditoren pivoxyl in an organic solvent chosen from ethylene glycol, propylene glycol, acetone, methyl ethyl ketone, methyl iso-butyl ketone, tetrahydrofuran, dioxane, acetonirile, a lower alkyl ester of acetic acid, particularly methyl acetate, ethyl acetate, and n-propyl acetate, methylene chloride and chloroform, as well as mixed solvents of two or more of them, and the alkanol used in the step (e) is chosen from methanol, ethanol, n-propanol, iso-propanol, n-butanol, iso-butanol, sec-butanol, tert-butanol, n-amyl alcohol, iso-amyl alcohol, sec-amyl alcohol and tert-amyl alcohol, as well as mixed solvents of two or more of them.

6. A process according to claim 3, in which the step (c) of incubating the solution of Cefditoren pivoxyl containing the seed crystal, as well as the steps (d) and (f) of concentrating the solution of Cefditoren pivoxyl are effected at a temperature of not higher than 10° C.

* * * * *